(12) United States Patent
Mazzetti et al.

(10) Patent No.: US 9,629,518 B2
(45) Date of Patent: Apr. 25, 2017

(54) CONTACTLESS CAMERA CONNECTION SYSTEM

(71) Applicant: Arthrex, Inc., Naples, FL (US)

(72) Inventors: Michael Mazzetti, Santa Barbara, CA (US); Steven A. Riley, Summerland, CA (US); David D'Alfonso, Gaviota, CA (US)

(73) Assignee: ARTHREX, INC., Naples, FL (US)

( * ) Notice: Subject to any disclaimer, the term of this patent is extended or adjusted under 35 U.S.C. 154(b) by 393 days.

(21) Appl. No.: 14/140,407

(22) Filed: Dec. 24, 2013

(65) Prior Publication Data
US 2014/0184771 A1 Jul. 3, 2014

Related U.S. Application Data

(60) Provisional application No. 61/746,411, filed on Dec. 27, 2012.

(51) Int. Cl.
| | | |
|---|---|---|
| *A61B 1/00* | (2006.01) | |
| *H02J 5/00* | (2016.01) | |
| *A61B 1/04* | (2006.01) | |

(52) U.S. Cl.
CPC ...... *A61B 1/00105* (2013.01); *A61B 1/00016* (2013.01); *A61B 1/00029* (2013.01); *A61B 1/00124* (2013.01); *A61B 1/042* (2013.01); *H02J 5/00* (2013.01)

(58) Field of Classification Search
CPC ............ A61B 1/00016; A61B 1/00029; A61B 1/00105; A61B 1/00124; A61B 1/042; H02J 5/00
See application file for complete search history.

(56) References Cited

U.S. PATENT DOCUMENTS

| | | | |
|---|---|---|---|
| 2007/0060789 A1 | 3/2007 | Uchimura et al. | |
| 2009/0137871 A1* | 5/2009 | Matsumoto | A61B 1/00041 600/117 |
| 2010/0097453 A1* | 4/2010 | Endo | A61B 1/00016 348/65 |

(Continued)

FOREIGN PATENT DOCUMENTS

| | | |
|---|---|---|
| EP | 1721568 | 11/2006 |
| EP | 2478825 | 7/2012 |

(Continued)

OTHER PUBLICATIONS

Ansah et al., Comparing Wireless N (IEEE 802.11n) and Wireless G (IEEE 802.11g) Standards in terms of Performance and Reliability, Jul. 2011, WCE, Proceedings of the World Congress on Engineering 2011 vol. II.*

(Continued)

*Primary Examiner* — Peter D Le
(74) *Attorney, Agent, or Firm* — Karish & Bjorgum, PC (57) ABSTRACT

A camera system having a camera head with an imaging device and a first connector; a camera control unit with a processor and a second connector configured to removably engage the first connector; and wherein the first connector and the second connector are configured to allow for contactless transfer of data from the camera head to the camera control unit and contactless transfer of power from the camera control unit to the camera head.

14 Claims, 10 Drawing Sheets

(56) References Cited

U.S. PATENT DOCUMENTS

2010/0179384 A1 7/2010 Hoeg et al.
2013/0082647 A1* 4/2013 Yoon .................. H02J 5/005
                                                              320/108

FOREIGN PATENT DOCUMENTS

WO    2008063565    5/2008
WO    2010049796    5/2010

OTHER PUBLICATIONS

Perahia et al., Gigabit Wireless LANs: an overview of IEEE 802.11ac and 802.11ad, Jul. 2011, ACM SIGMOBILE Mobile Computing and Communications Review, vol. 15 Issue, pp. 23-33.*
International Search Report and Written Opinion, Mailed Jan. 20, 2015.

* cited by examiner

CONTACTLESS CAMERA CONNECTION SYSTEM

CROSS REFERENCE TO RELATED APPLICATION

This application claims priority of U.S. Provisional Patent Application No. 61/746,411, filed on Dec. 27, 2012, entitled CONTACTLESS VIDEO CAMERA CONNECTOR, the entire contents of which are hereby incorporated herein by reference.

BACKGROUND OF THE INVENTION

The present invention relates to devices used in endoscopic surgery and, more particularly, to a system for transferring power and data for a camera used in endoscopic surgery.

The connector used between an endoscopic camera head and a corresponding camera control unit should be: waterproof, able to survive numerous autoclave sterilization cycles, able to survive numerous Sterrad sterilization cycles, reliable and easy to connect and disconnect. The connector should also allow for multiple high rate channels of data transmission and provide for the transmission of several watts of DC power. Traditional connector gold contact designs are the industry standard, but degrade with repeated sterilization processing that contaminates and corrodes the contact surfaces.

There are some known methods for sending digital data through contactless connectors as well as techniques for wireless DC power transfer. However, prior art methods suffer from at least one of the following problems: they do not address the need for high safety isolation, multiple parallel high rate data channels or sealed/autoclave sterilization compatibility.

Thus, there is a need for an improved camera connector that remedies the shortcomings of the prior art.

SUMMARY

This invention addresses the shortcomings of the prior art with contactless power and data coupling at the connector interface. In addition, this invention achieves electrical isolation and safety protection between the patient connected camera head and the camera control unit.

A camera system according to an embodiment of the present invention has a camera head with an imaging device and a first connector; and a camera control unit with a processor; and a second connector configured to removably engage the connector. The first connector and the second connector are configured to allow for contactless transfer of data from the camera head to the camera control unit and contactless transfer of power from the camera control unit to the camera head.

The camera head may also have an illumination system; and the first connector and the second connector may be configured for contactless transfer of power for the illumination system. The first connector and the second connector may also be configured to allow for contactless transfer of data from the camera control unit to the camera head. Optionally, the first connector has at least one power receiver coupled to at least one power receiver coil; and the second connector has at least one power transmitter and at least one power transmitter coil; and wherein power is transferred between the first connector and the second connector using magnetic field coupling between the at least one power transmitter coil and the at least one power receiver coil. Optionally, the first connector has two power receivers, each power receiver being coupled to a separate power receiver coil; and the second connector has at least two power transmitters, each power transmitter being coupled to a separate power transmitter coil.

In an embodiment, data is transferred using near field energy. The first connector may have a plurality of data transfer surfaces and may simultaneously transmit data using multiple data paths. In an additional embodiment, the first connector transmits data using a radio transmitter and the second connector receives data using a radio receiver. The first connector may have a plurality of extremely high frequency radio transmitters and be configured to transmit at least 4 channels of data simultaneously. The second connector may have a plurality of high frequency radio receivers and be configured to receive at least 4 channels of data simultaneously. Optionally, each data channel transfers data at a rate of at least about 0.5 Gbs. Optionally, each data channel transfers data at a rate of at least about 2.5 Gbs. In an embodiment, the second connector has a retractable plunger and the first connector has a detent; and wherein the retractable plunger is engageable with the detent to maintain engagement of the first connector with the second connector.

In an embodiment, the first connector has a shield; and the second connector has a plate capacitor; and the first connector and the second connector are configured so that when the first connector is engaged with the second connector, the shield is positioned in electrical contact with the plate capacitor.

In an additional embodiment, the present invention is directed to a camera system having a camera head with: an imaging device; an illumination system; and a first connector further comprising at least one radio transmitter; at least one power receiver; and at least one power receiver coil coupled to the at least one power receiver. The camera system also has a camera control unit with: a processor; and a second connector configured to removably engage the first connector, the second connector further comprising at least one radio receiver; at least one power transmitter; and at least one power transmitter coil coupled to the at least one power transmitter. The first connector and the second connector are configured for contactless transfer of data between the camera head and the camera control unit using the at least one radio transmitter and the at least one radio receiver. The first connector and the second connector are configured for contactless power transfer from the camera control unit to the camera head using magnetic field coupling between the at least one power transmitter coil and the at least one power receiver coil.

Optionally, the first connector has at least one extremely high frequency radio transmitter and at least one extremely high frequency radio receiver, and the second connector has at least one extremely high frequency radio receiver and at least one extremely high frequency radio transmitter. The first connector and the second connector may be configured for simultaneously transmitting at least one channel of data from the camera head to the camera control unit and at least one channel of data from the camera control unit to the camera head. Preferably, each data channel transfers data at a rate of at least about 0.5 Gbs.

In an embodiment, the first connector has a shield; and the second connector has a plate capacitor; and the first connector and the second connector are configured so that when the first connector is engaged with the second connector, the shield is positioned in contact with the plate capacitor. Optionally, the second connector has a retractable plunger and the first connector has a detent; and wherein the retractable plunger is engageable with the detent to maintain engagement of the first connector with the second connector. The camera head may also have at least one wired interface allowing for programming and data access to the camera head.

In another embodiment, the present invention is directed to a method for contactless data and power transfer between a camera head and a camera control system. The method has the step of selecting a camera head with an imaging device; an illumination system; and a first connector further comprising a plurality of extremely high frequency radio transmitters; an extremely high frequency radio receiver; at least one power receiver; and at least one power receiver coil coupled to the at least one power receiver. The method further comprises the step of selecting a camera control unit with a processor; and a second connector configured to receive the connector, the second connector further comprising a plurality of extremely high frequency radio receivers; an extremely high frequency radio transmitter; at least one power transmitter; and at least one power transmitter coil coupled to the at least one power transmitter. The method further comprises the steps of connecting the first connector and the second connector; transferring data between the camera head and the camera control unit without direct contact using the extremely high frequency radio transmitters and receivers; and transferring power from the camera control unit to the camera head without contact using magnetic field coupling between the at least one power transmitter coil and the at least one power receiver coil.

BRIEF DESCRIPTION OF THE DRAWINGS

The features, aspects and advantages of the present invention will become better understood with regard to the following description, appended claims and accompanying figures wherein:

DETAILED DESCRIPTION

In the following description of the preferred embodiments, reference is made to the accompanying drawings which show by way of illustration specific embodiments in which the invention may be practiced. Wherever possible, the same reference numbers will be used throughout the drawings to refer to the same or like parts. It is to be understood that other embodiments may be utilized and structural and functional changes may be made without departing from the scope of the present invention.

Figure 1:
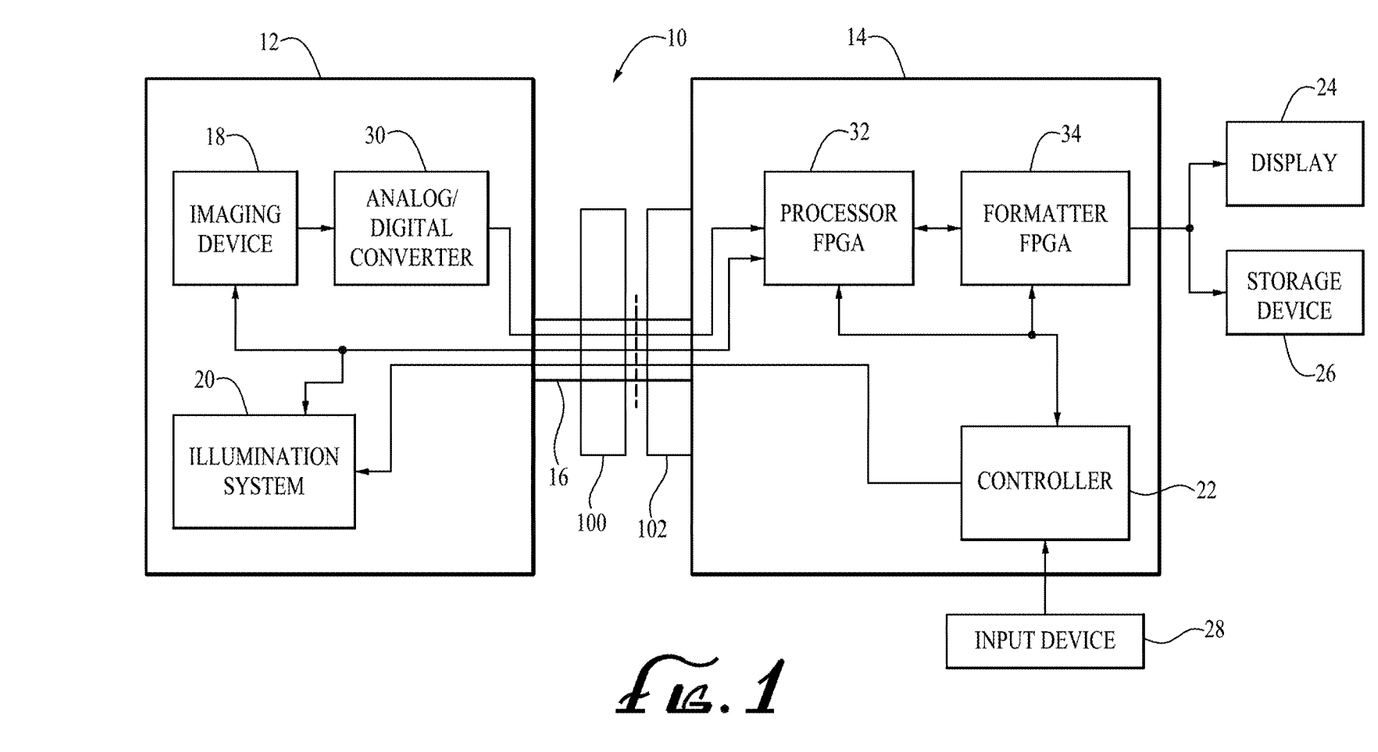
FIG. 1 is a schematic drawing of an endoscope system according to an embodiment of the present invention.

An endoscopic imaging system 10 according to an embodiment of the present invention is shown in FIG. 1. The endoscopic imaging system 10 allows for internal features of a body of a patient to be viewed without the use of traditional, fully invasive surgery. Additionally, the endoscopy system may be used for imaging of hard to reach parts of structures or in other applications where direct optical viewing is compromised.

The endoscopic imaging system 10 has a camera head 12 and a camera control unit 14. The camera head 12 is coupled to the camera control unit 14 via a cable 16 to facilitate data transfer between the camera head 12 and the camera control unit 14. The camera head 12 acquires image data and transmits it to camera control unit 14 to process a usable image. The camera head 12 may be used together with an endoscope or other medical instruments for transmitting image data. The camera head 12 may include one or more imaging devices 18, utilizing a variety of technology types. For example, the imaging devices may include one or more charge coupled device (CCD) sensors or complementary metal-oxide-semiconductor (CMOS) sensors. The camera head 12 may also include an illumination system 20.

The camera control unit 14 is preferably a programmable unit containing sufficient processing capacity to accommodate a wide range of control, user interface and image acquisition/processing functions. The camera control unit 14 has a controller 22 and runs program applications providing for a variety of capabilities. For instance, an image capture and display capability allows for both display of a live feed of an image through a display 24 coupled to the camera control unit 14, as well as image capture. Captured images may be stored to an external storage device 26 coupled to the camera control unit 14 such as via a Universal Serial Bus interface. Alternatively, the external storage device 26 may be a storage device accessible via the Internet. Additionally, the controller 22 may receive information and other input from one or more input devices 28.

In an embodiment, digital data, including image data, is transmitted from the imaging device 18 to the camera control unit 14. If the imaging devices 18 in the camera head 12 do not produce digital data, then the camera head may have an analog/digital converter 30 for converting analog data to digital data. The digital data is then passed to the camera head where the video is processed, such as in a processor field programmable gate array (FPGA) 32. The processed video is then formatted into various display formats, such as by a formatter FPGA 34. The formatter FPGA 34 may also overlay information, such as patient and/or doctor information, onto the video. The formatted video may be converted back to an analog signal for display. The formatted video is sent to the display 24 and/or the storage device 26.

The camera control unit 14 issues commands to the camera head 12 to adjust its operating characteristics and the camera head 12 may send confirmation to the camera control unit 14 that it received the commands. The processor FPGA 32 and the controller 22 may communicate with a shutter driver either in the camera control unit or the camera head to control the exposure period of the imaging device. Additionally, the processor FPGA 32 and the controller 22 may communicate with a light source driver either in the camera control unit or the camera head to control power to an illumination source of the illumination system 20.

With reference to FIGS. 1 to 7, the present invention, according to an embodiment, is directed to a connectable contact free interface for transmission of both multiple channel high speed data and DC power between the camera head 12 and the camera control unit 14. The camera head has a camera head connector 100 and the camera control unit has a camera control unit connector 102. Preferably, the camera head connector 100 is a male plug and the camera control unit connector 102 is a female receptacle. Optionally, the camera control unit connector 102 is on a cable connectable to the camera control unit 14. Alternatively, the camera head connector 100 may be configured as a female receptacle for receipt of a male plug on a cable connectable to the camera control unit 14. Optionally, the camera head connector 100 and camera control unit connector 102 are configured to be placed in close proximity, such as side by side, for data and/or power transfer.

Figure 2:
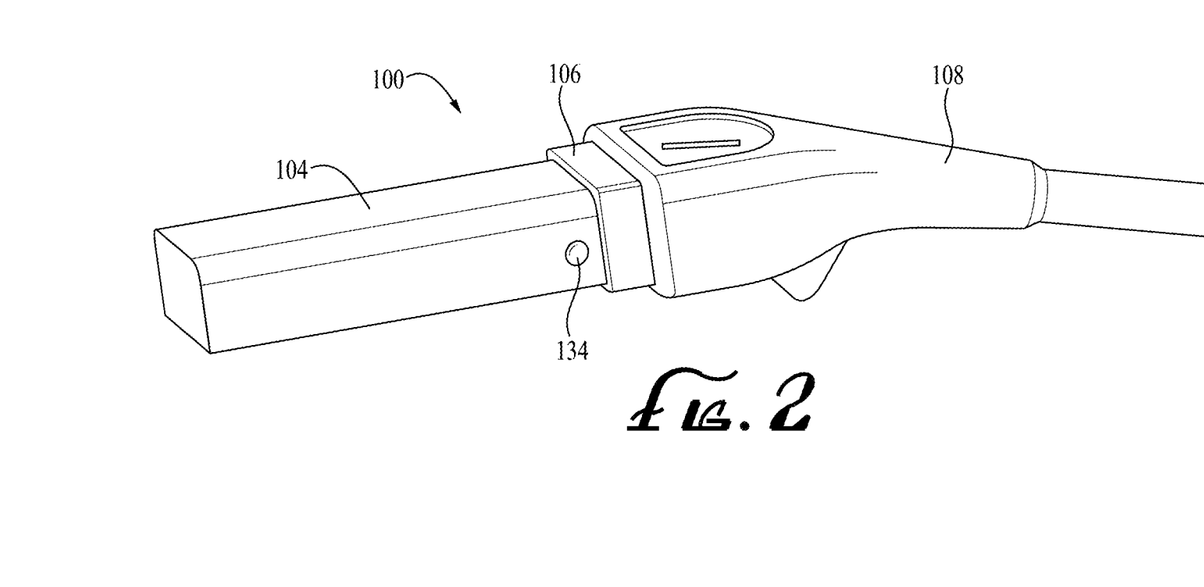
FIG. 2 is a perspective elevation view of a camera head connector according to a first embodiment of the present invention.

Preferably the camera head connector 100 and the camera control unit connector 102 are shaped to allow for one handed and sightless connection so that an operator can connect the camera head 12 to the camera control unit 14 by feel. The camera head connector 100 may be, for example, cylindrically shaped or multi-faceted, such as pentagonal or hexagonal. In an embodiment, as shown in FIG. 2, the camera head connector 100 has a plastic cover 104 surrounding circuitry inside the connector. The camera head connector 100 also has an exposed metal shield 106 for grounding and electrical isolation of the connector as explained below. The camera head connector 100 also has a grip 108 configured so that a user, such as a surgeon or technician wearing gloves, may grip the connector. A plug board 110 is mounted inside the plastic cover 104.

Figure 3:
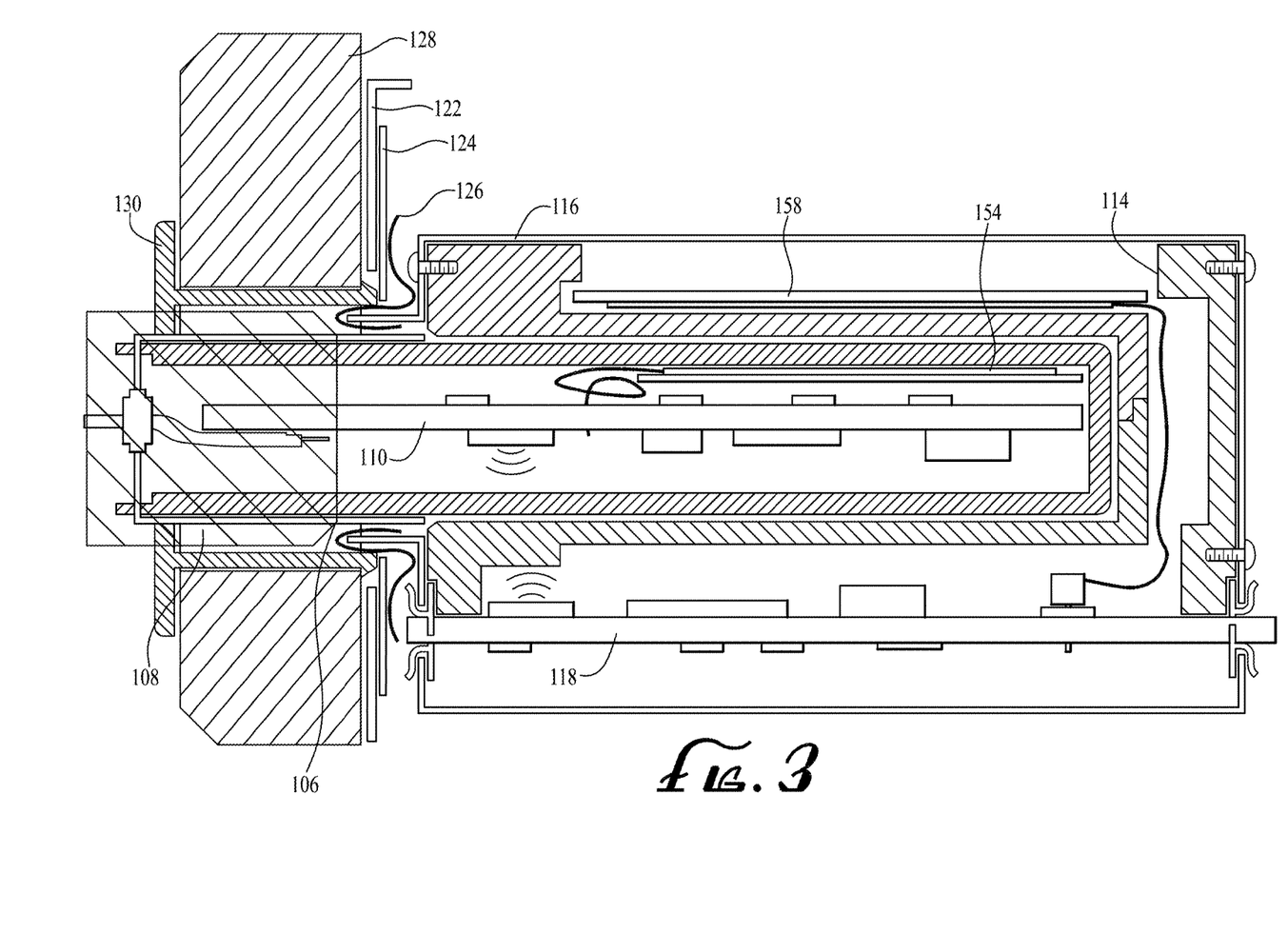
FIG. 3 is a perspective side cross-sectional view of a camera head connector coupled to a camera control unit connector according to the first embodiment of the present invention.
Figure 4:
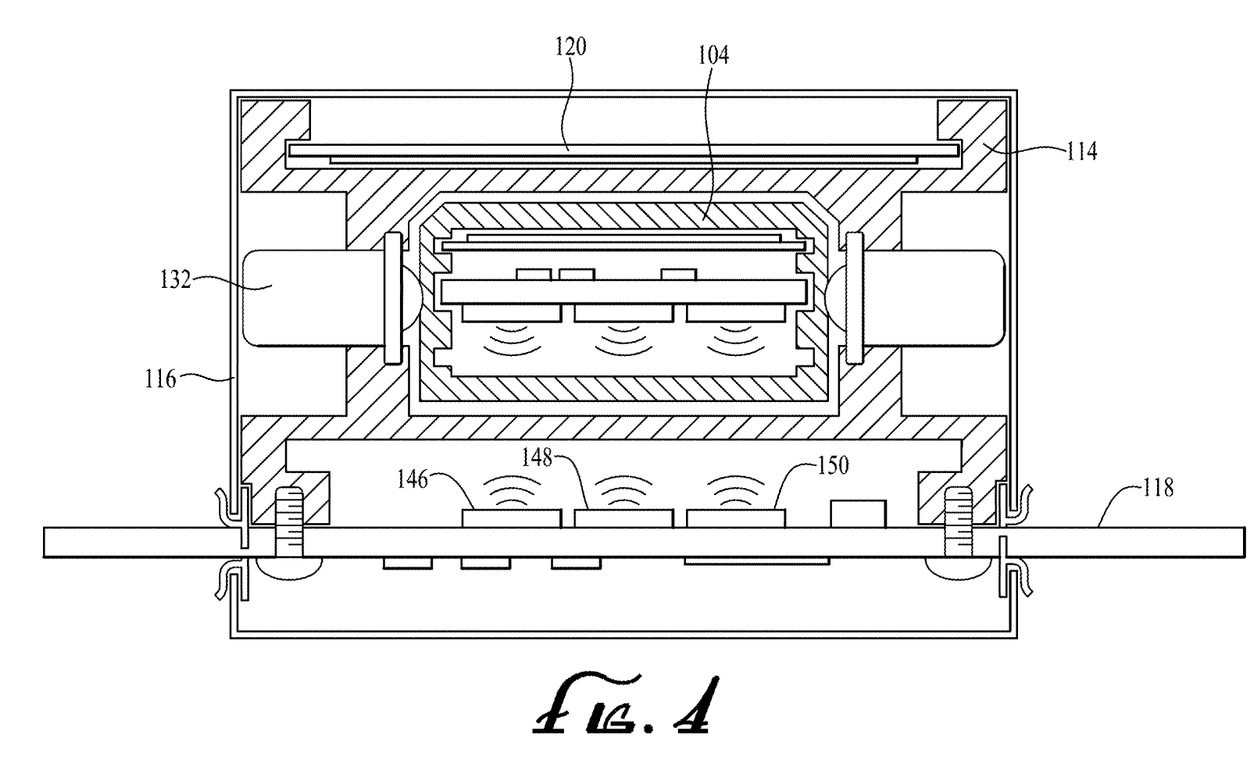
FIG. 4 is a perspective end cross-sectional view of a camera head connector coupled to a camera control unit connector according to the first embodiment of the present invention.

With reference to FIGS. 3 and 4, the camera control unit connector 102 has a body 114 surrounded by a shield box 116 to prevent magnetic radiation to other CCD circuits or the environment. In an embodiment, the body 114 is made of molded plastic and the shield box 116 is made of metal. The body 114 is coupled to an isolation board 118. The shield box 116 is coupled to the isolation board 118 and substantially surrounds the isolation board. The shield box 116 is contained in the camera control unit chassis 122. A capacitor 124, such as a plate capacitor, is mounted between the camera control unit chassis 122 and the shield box 116.

An electromagnetic compatibility (EMC) spring clip 126 is mounted between the capacitor 124 and the shield box 116. The EMC spring clip 126 is configured to engage the exposed metal shield 106 of the camera head connector 100. The shield box 116 and the exposed metal shield 106 of the camera head connector 100 are connected to the camera control unit chassis 122 through the capacitor 124, rather than directly, to maintain safe electrical isolation from the patient, to control undesired electromagnetic emission and to protect the camera system from electromagnetic interference.

The camera control unit 14 has a face plate 128 coupled to the chassis 122. A receiver 130 passes through a hole in the face plate 128, the chassis 122 and the shield box 116. The plastic receiver 130 is configured to receive the camera head connector 100 and position the camera head connector inside the body 114. In an embodiment, the camera control unit connector 102 has a retractable plunger 132 that removeably engages with a detent 134 in the plastic cover 104 of the camera head connector 100. The retention plunger 132 may also be coupled to an engagement sensor (not shown) to commence communication or power transfer upon engagement of the retention plunger 132 with the detent 134. Alternatively, the camera head connector 100 may be removeably held in the camera control unit connector 102 by magnets positioned on the camera head connector and the camera control unit connector. Additionally, the isolation board may be coupled to an opto-interrupter 136 to commence communication or power transfer upon successful insertion of the camera head connector 100 into the camera control unit connector 102.

Data Transfer

Figure 5:
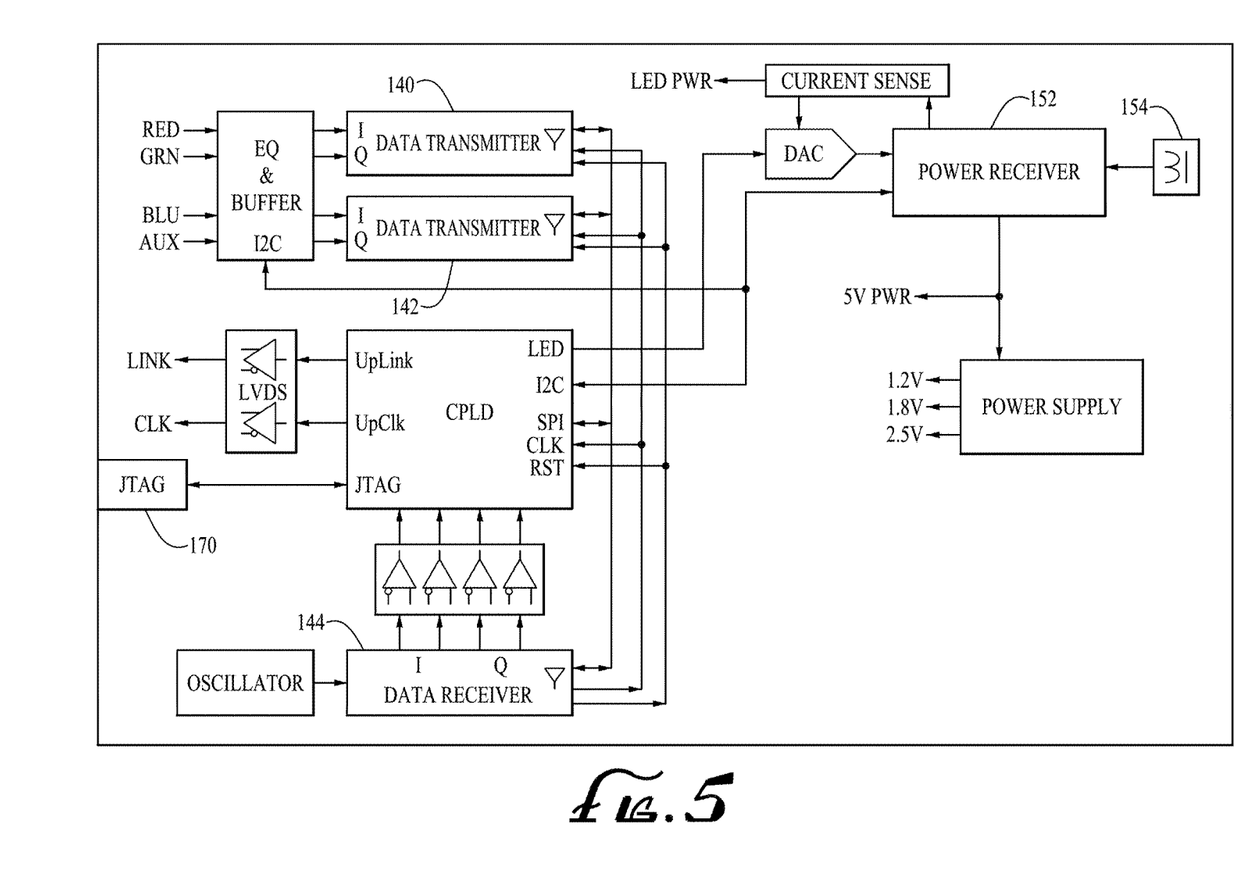
FIG. 5 is a schematic diagram of a plug board usable in the camera head connector of the first embodiment of the present invention.
Figure 6:
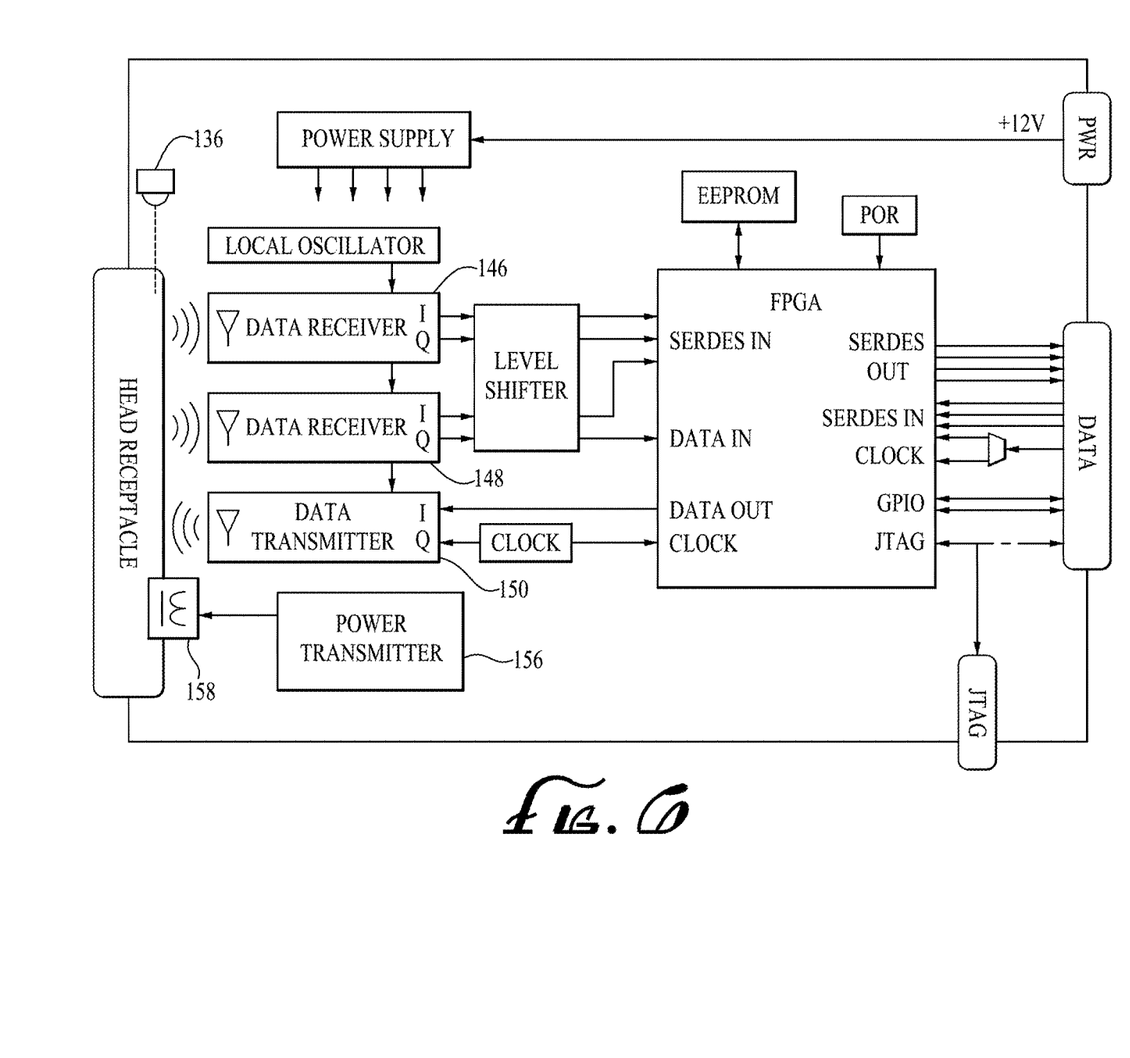
FIG. 6 is a schematic diagram of an isolation board usable in the camera control unit connector of the first embodiment of the present invention.
Figure 7:
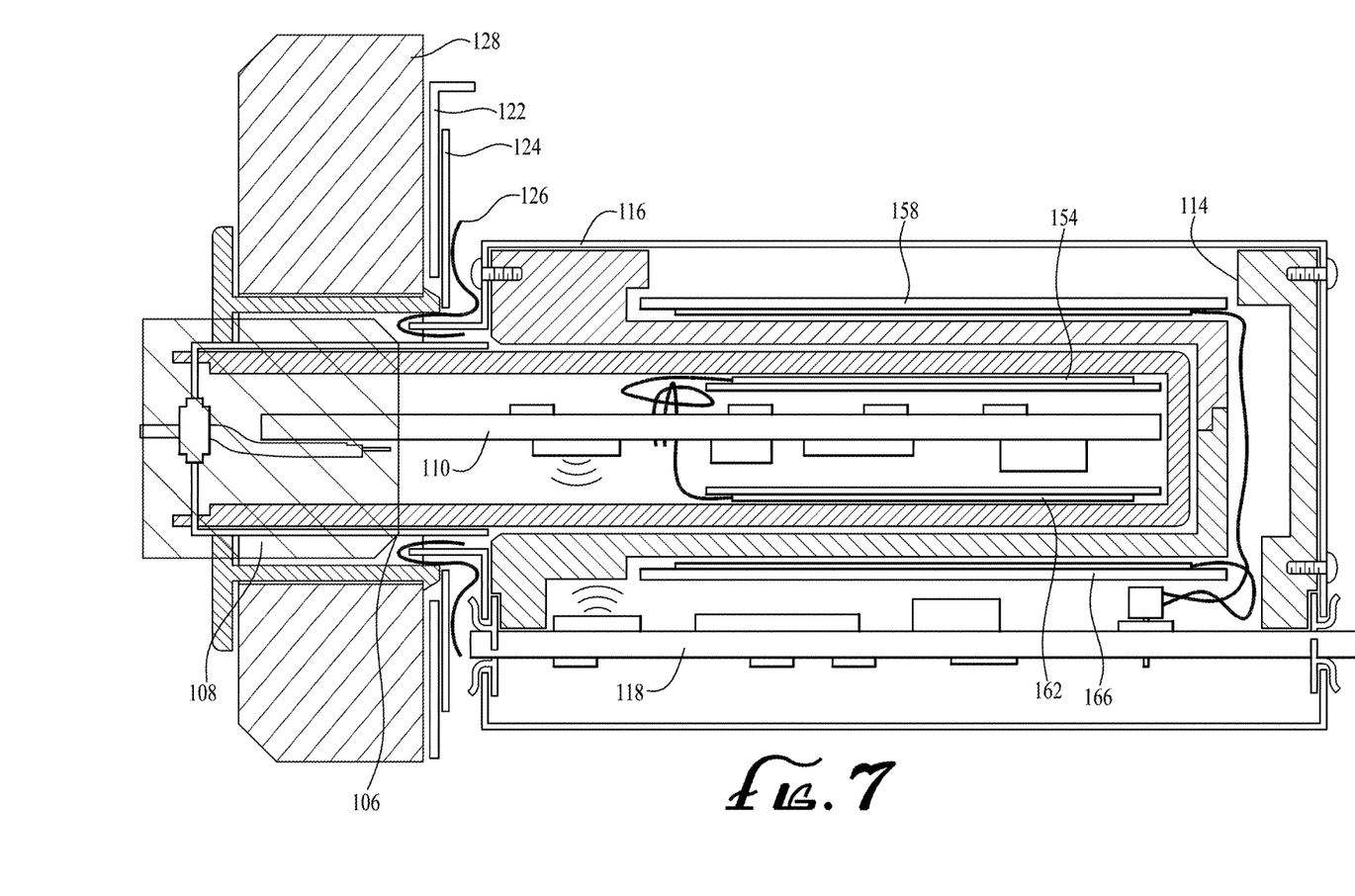
FIG. 7 is a perspective side cross-sectional view of a camera head connector coupled to a camera control unit connector according to a second embodiment of the present invention.
Figure 8:
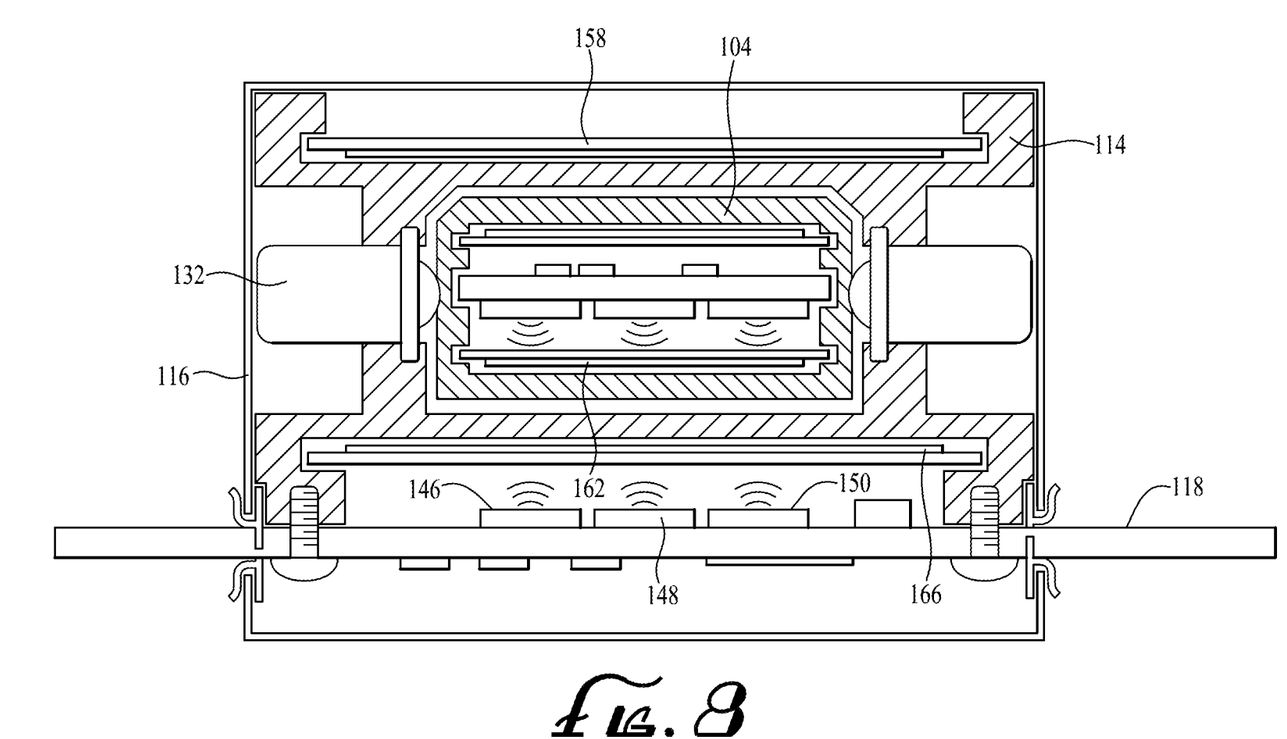
FIG. 8 is a perspective end cross-sectional view of a camera head connector coupled to a camera control unit connector according to the second embodiment of the present invention.
Figure 9:
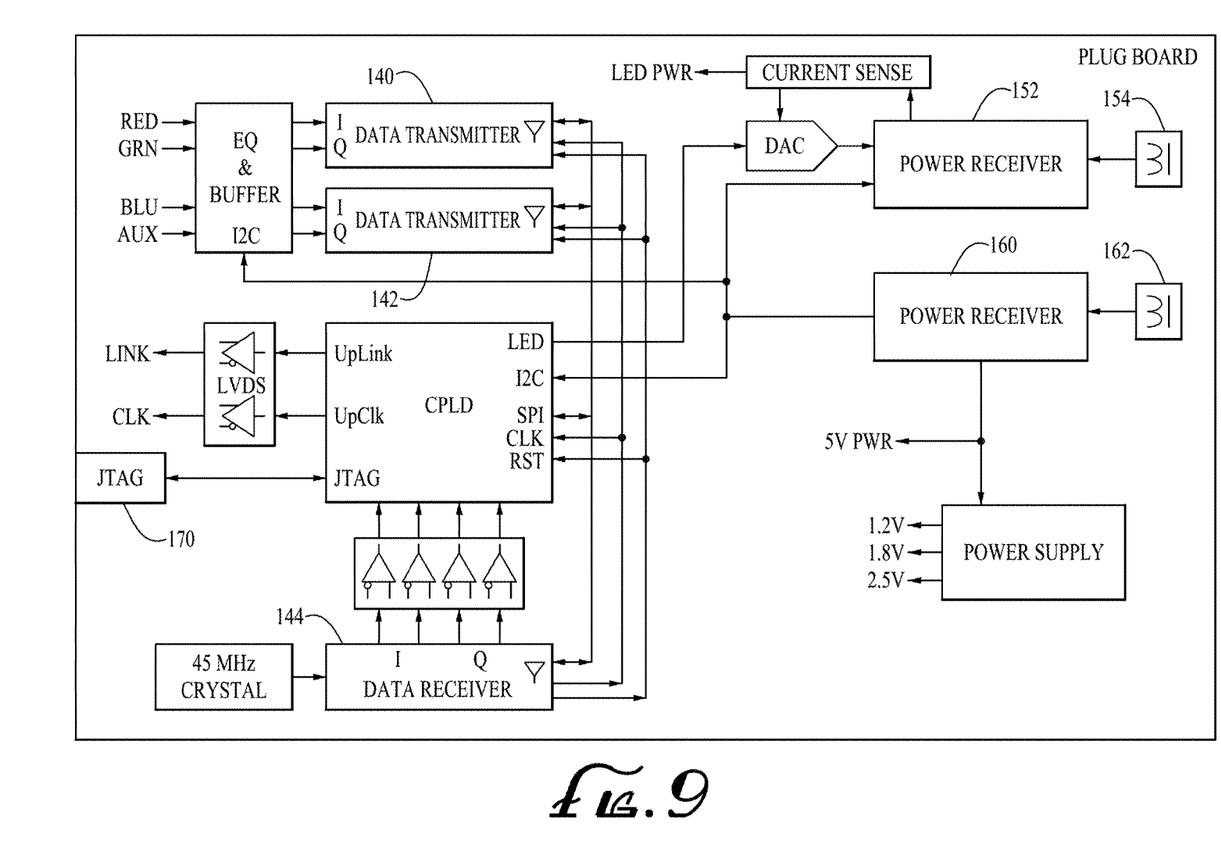
FIG. 9 is a schematic diagram of a plug board usable in the camera head connector of the second embodiment of the present invention.
Figure 10:
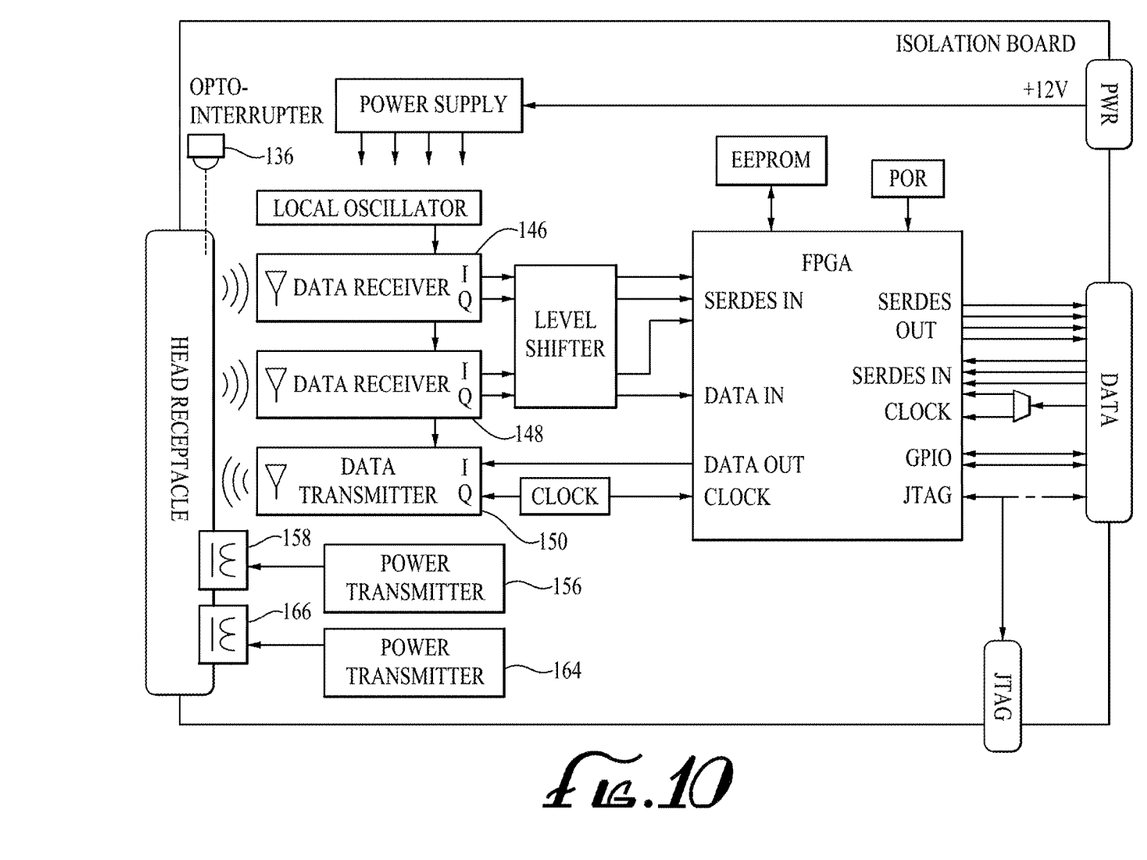
FIG. 10 is a schematic diagram of an isolation board usable in the camera control unit connector of the second embodiment of the present invention.

The plug board 110 has first and second plug board data transmitters 140, 142 and a plug board data receiver 144. The isolation board has first and second isolation board data receivers 146, 148 and an isolation board data transmitter 150. Data transmission is preferably conducted wirelessly via extremely high frequency (e.g. 60 Ghz) radio communication. Preferably, each transmitter can accept two 2 gigabit per second data streams using quadrature modulation for 60 GHz transmission. Data transmitters and receivers usable with the present invention include, for example, PRS1021 transceivers from Peraso Products, 144 Front Street West, Suite 685, Toronto, Canada. A plurality of radio frequencies being used for simultaneous transmission and reception.

In an embodiment of the present invention, there are four data signals that leave the camera head, pass through some signal conditioning equalizers and buffers, then into the transmitters. Red and green channel information from the camera head imaging device 18 is transmitted from the first plug board data transmitter 140 to the first isolation board data receiver 146. Blue channel data along with additional camera head data, such as for example, button press, temperature sensor and acceleration sensor data, is transmitted from the second plug board data transmitter 142 to the second isolation board data receiver 148. Data from the camera control unit for the camera head 12, such as for example, timing and control for image sensor and illumination system operation, is transmitted from the isolation board data transmitter 150 to the plug board data receiver 144.

The use of extremely high frequency radio communications (e.g. 60 Ghz) along with the use of multiple (for example 3 or more) different sets of transmitters and receivers allows for very robust data transfer, thereby allowing for uncompressed or lightly compressed high resolutions image data from the camera head. Additionally, the electro-magnetic radio energy is confined within the shield box 116. As will be understood by those of skill in the art, different wireless transfer protocols and different numbers of transmitters and receivers may be selected depending on the picture quality and data transfer needs of the system. For example, the system may have a single plug board data transmitter and a single isolation board data receiver, and may transmit one channel of data.

Power Transfer

As shown in FIGS. 3 to 6, the plug board 110 has a power receiver 152 electrically coupled to a receiver coil 154 and the isolation board 118 has a power transmitter 156 electrically coupled to a transmitter coil 158. Power transfer is done via inductive coupling at short distances (typically a few millimeters or less). The transmitter coil 158 is coupled with the receiver coil 154. AC current in the transmitter coil 158 generates a magnetic field that induces a voltage in the receiver coil 154. The voltage in the receiver coil 154 is used to power the camera head 12. The magnetic field is concentrated in a small area between the transmitter coil 158 and the receiver coil 154. A power receiver usable in the present invention is Part No. IDTP9021 by Integrated Device Technology, Inc., 6024 Silver Creek Valley Road, San Jose, Calif. 95138. A power transmitter usable in the present invention is Part No. IDTP9031 by Integrated Device Technology, Inc., 6024 Silver Creek Valley Road, San Jose, Calif. 95138.

Preferably, the transmitter and receiver coils are flat and round. A transmitter coil usable in the present invention is a WE-WPCC wireless power charging coil by Wurth Electronics ICS, Inc., 7496 Webster St., Dayton, Ohio 45414. A receiver coil usable in the present invention is Part No. IWAS-3827EC-50 by Vishay Americas, One Greenwich Place, Shelton, Conn. 06484. Preferably, to limit interference, the data transmitters and receivers are mounted as far away as possible from the power transmitter coil and the power receiver coil.

In an additional embodiment of the present invention, as shown in FIGS. 7 to 10, the plug board 110 contains a second power receiver 160 coupled to a second receiver coil 162 and the isolation board 118 has a second power transmitter 164 coupled to a second transmitter coil 166. The presence of more than one power transmitter and receiver system allows for separate power systems for different camera head components. For example, one power receiver may be used to power the imaging device components and a second power receiver may be used to power the illumination system. The number of power receivers depends on the power transfer capabilities of the power transmission components and the power requirements of the camera head components.

In an alternative embodiment of the present invention, data is transferable from the camera head 12 to the camera control unit 14 without direct electrical contact by coupling near field energy across a short distance between a transfer surface in the camera head connector 100 and a corresponding receiver surface in the camera control unit connector 102. In an embodiment, the data transfer surface is a transmitter with a near-field antenna, such as a fractal antenna. The antenna may be mounted in a flexible Kapton wing.

Preferably, there are a plurality of data paths and transmitters, and the near field regions of each of the multiple data paths are separated so that cross talk does not threaten signal integrity across the interface. In an embodiment, the camera head connector 100 is pentagonal and each side contains a separate data transfer surface. In an embodiment, there are four data paths for data from the camera head 12 to the camera control unit 14, one data path for red image data, one data path for green image data, one data path for blue image data, and one data path for additional data. Preferably, each data path has a transfer rate of greater than about 0.5 Gbs and more preferably, greater than about 2.5 Gbs.

In an embodiment, the camera head connector 100 has at least one wired interface, such as a Joint Test Action Group (JTAG) interface 170 allowing for direct programming and data access to circuitry in the camera head connector. Preferably, the camera head 12 may be disconnected from the cable 16 as a service convenience should the cable be damaged. At this connection point the JTAG interface 170 could be exposed to allow access to the camera head circuitry and to the plug circuitry. For example, the JTAG interface 170 may be used to re-write memory in the camera head, should camera head firmware become corrupted. Additionally, the JTAG interface 170 may be used to reconfigure and reprogram hardware in the connector 100.

An alternative solution for contactless high speed data transmission is conversion to optical energy. This greatly reduces crosstalk but has the added complication that the optical interface must be very clean. The fiber is usually quite small so a single speck of contamination can block the signal. To address this vulnerability a lens, in the form of a glass sphere, is used to expand the optical beam at the interface and then converge it again at the other side.

In additional embodiment of the present invention the power delivery and data transfer systems may be decoupled. For example, the camera head 12 may have a battery to power the imaging device 18 and any present illumination system 20, thereby eliminating the need for power transfer during operation of the camera head. The battery may be charged prior to use using magnetic field charging, such as described above, by placing the camera head connector 100 and the camera control unit connector 102 in close proximity. Thereafter the camera head connector 100 and the camera control unit connector 102 may be moved apart. Data transfer using, for example extremely high frequency (e.g. 60 Ghz) radio communication as described above, can be done over longer distances than magnetic field charging, and the camera head connector 100 and the camera control unit connector 102 may be located farther apart, such as two or more feet apart.

Preferably the camera head connector 100 is constructed from high temperature material such as plastic, ceramic, or glass to both seal and electrically insulate internal conductors from surface exposure. Thinner encapsulation improves electrical coupling, but a thicker covering provides a more dependable seal and greater electrical safety isolation.

The contactless camera connector system of the present invention has numerous advantages. The connector has improved reliability. Repeated autoclave sterilization cycles cause contaminants to build up on ordinary contact type connectors that lead to degraded camera performance. Without electrical contacts this connector may be connected and disconnected and subjected to autoclave sterilization over 1000 times, and preferably over 2000 times, and therefore provides for long service. A contact free design allows for a smooth outer surface with few crevices or openings to trap bio-debris making sterilization and cleaning processes more effective.

There is disclosed in the above description and the drawings, a contactless camera connector system that fully and effectively overcomes the disadvantages associated with the prior art. However, it will be apparent that variations and modifications of the disclosed embodiments may be made without departing from the principles of the invention. The presentation of the preferred embodiments herein is offered by way of example only and not limitation, with a true scope and spirit of the invention being indicated by the following claims.

Any element in a claim that does not explicitly state "means" for performing a specified function or "step" for performing a specified function, should not be interpreted as a "means" or "step" clause as specified in 35 U.S.C. §112.

What is claimed is:
1. A camera system used with an endoscope comprising:
a camera head further comprising:
   an imaging device; and
   a first connector, the first connector comprising a metal shield and a plurality of extremely high frequency radio transmitters configured to transmit a plurality of channels of data simultaneously;
a camera control unit comprising:
   a processor; and
   a second connector configured to removably engage the first connector, the second connector comprising a capacitor and a plurality of high frequency radio receivers configured to receive a plurality of channels of data simultaneously; and
   wherein the first connector and the second connector are configured to allow for contactless transfer of uncompressed high definition video from the camera head to the camera control unit and contactless transfer of power from the camera control unit to the camera head; and
   wherein the first connector and the second connector are configured so that when the first connector is engaged with the second connector, the shield is physically coupled to the capacitor.

2. The camera system of claim 1 wherein the camera head further comprises an illumination system; and the first connector and the second connector are configured for contactless transfer of power for the illumination system.

3. The camera system of claim 1 wherein the first connector further comprises at least one power receiver coupled to at least one power receiver coil; and wherein the second connector further comprises at least one power transmitter and at least one power transmitter coil; and wherein power is transferred between the first connector and the second connector using magnetic field coupling between the at least one power transmitter coil and the at least one power receiver coil.

4. The camera system of claim 3 wherein the first connector further comprises two power receivers, each power receiver being coupled to a separate power receiver coil; and wherein the second connector further comprises at least two power transmitters, each power transmitter being coupled to a separate power transmitter coil.

5. The camera system of claim 1 wherein data is transferred using near field energy.

6. The camera system of claim 5 wherein the first connector further comprises a plurality of data transfer surfaces and simultaneously transmits data using multiple data paths.

7. The camera system of claim 1 wherein each data channel transfers data at a rate of at least about 0.5 Gbs.

8. The camera system of claim 1 wherein each data channel transfers data at a rate of at least about 2.5 Gbs.

9. The camera system of claim 1 wherein the second connector further comprises a retractable plunger and the first connector further comprises a detent; and wherein the retractable plunger is engageable with the detent to maintain engagement of the first connector with the second connector.

10. A camera system used with an endoscope comprising:
a camera head further comprising:
   an imaging device;
   an illumination system; and
   a first connector further comprising:
      a plurality of extremely high frequency radio transmitters configured to transmit a plurality of channels of data simultaneously;
      at least one extremely high frequency radio receiver;
      at least one power receiver;
      at least one power receiver coil coupled to the at least one power receiver; and
      a metal shield;
a camera control unit comprising:
   a processor; and
   a second connector configured to removably engage the first connector, the second connector further comprising:
      a plurality of high frequency radio receivers configured to receive a plurality of channels of data simultaneously;
      at least one extremely high frequency radio transmitter;
      at least one power transmitter;
      at least one power transmitter coil coupled to the at least one power transmitter; and a capacitor; and
   wherein the first connector and the second connector are configured for contactless transfer of uncompressed high definition video between the camera head and the camera control unit using the at least one radio transmitter and the at least one radio receiver;
   wherein the first connector and the second connector are configured for contactless power transfer from the camera control unit to the camera head using magnetic field coupling between the at least one power transmitter coil and the at least one power receiver coil; and
   wherein the first connector and the second connector are configured so that when the first connector is engaged with the second connector, the shield is physically coupled to the capacitor.

11. The system of claim 10 wherein each data channel transfers data at a rate of at least about 0.5 Gbs.

12. The camera system of claim 10 wherein the second connector further comprises a retractable plunger and the first connector further comprises a detent; and wherein the retractable plunger is engageable with the detent to maintain engagement of the first connector with the second connector.

13. The camera system of claim 10 wherein the camera head further comprises at least one wired interface allowing for programming and data access to the camera head.

14. A method for contactless data and power transfer between a camera head and a camera control system used with an endoscope, the method comprising:
selecting a camera head further comprising:
   an imaging device;
   an illumination system; and
   a first connector further comprising:
      a plurality of extremely high frequency radio transmitters configured to transmit a plurality of channels of data simultaneously;
      an extremely high frequency radio receiver;
      at least one power receiver; at least one power receiver coil coupled to the at least one power receiver; and
      a metal shield;
selecting a camera control unit comprising:
   a processor; and
   a second connector configured to removably engage the first connector, the second connector further comprising:
      a plurality of extremely high frequency radio receivers configured to receive a plurality of channels of data simultaneously;
      an extremely high frequency radio transmitter;
      at least one power transmitter;

at least one power transmitter coil coupled to the at least one power transmitter; and a capacitor;

engaging the first connector and the second connector so that when the first connector is engaged with the second connector, the shield is coupled to capacitor by an electromagnetic compatibility clip;

transferring uncompressed high definition video between the camera head and the camera control unit without direct contact using the extremely high frequency radio transmitters and receivers; and transferring power from the camera control unit to the camera head without contact using magnetic field coupling between the at least one power transmitter coil and the at least one power receiver coil.

* * * * *